United States Patent
Prasser et al.

(12)

(10) Patent No.: US 6,314,373 B1
(45) Date of Patent: Nov. 6, 2001

(54) GRID SENSOR FOR DETERMINING THE CONDUCTIVITY DISTRIBUTION IN FLOW MEDIA AND PROCESS FOR GENERATING MEASUREMENT SIGNALS

(75) Inventors: Horst-Michael Prasser; Jochen Zschau; Arnd Boettger, all of Dresden (DE)

(73) Assignee: Forschungszentrum Rossendorf e.V., Schoenfeld-Weissig (DE)

( * ) Notice: Subject to any disclaimer, the term of this patent is extended or adjusted under 35 U.S.C. 154(b) by 0 days.

(21) Appl. No.: 09/254,015

(22) PCT Filed: Nov. 17, 1997

(86) PCT No.: PCT/DE97/02683

§ 371 Date: May 7, 1999

§ 102(e) Date: May 7, 1999

(87) PCT Pub. No.: WO98/23947

PCT Pub. Date: Jun. 4, 1998

(30) Foreign Application Priority Data

Nov. 27, 1996 (DE) .............................................. 196 49 011

(51) Int. Cl.[7] .......................... G01N 27/00; G06F 19/00
(52) U.S. Cl. ............................ 702/23; 702/50; 73/61.44; 73/61.52; 324/691; 324/693; 324/722
(58) Field of Search .............................. 702/23, 50, 100, 702/128; 73/61.44, 61.52, 61.64, 61.53; 324/690–694, 719–722

(56) References Cited

U.S. PATENT DOCUMENTS

| 4,644,263 | * | 2/1987 | Johnson | 73/61.44 |
|---|---|---|---|---|
| 4,656,427 | | 4/1987 | Dauphinee . | |
| 4,777,431 | * | 10/1988 | Day et al. | 324/663 |
| 4,833,413 | | 5/1989 | Head . | |
| 5,210,499 | * | 5/1993 | Walsh | 324/649 |
| 5,641,893 | * | 6/1997 | Penn et al. | 73/61.53 |

FOREIGN PATENT DOCUMENTS

| 3201799C1 | 8/1983 | (DE) . |
|---|---|---|
| 4041160C2 | 7/1991 | (DE) . |
| 2614104A | 10/1988 | (FR) . |

OTHER PUBLICATIONS

A. V. Ploshinskii: "Primary Sensors With Hydrodynamic Smoothing for Conductometry on Turbulent Flows", Measurement Techniques, vol. 29, No. 3, 1986, New York US, pp. 250–252, XP002061552.

M. Boden, N. Reinecke, D. Mewes: "Measurement of two–dimensional phase distributions using a wire–mesh sensor", Proc. ECAPT, Oporto, Portugal, 1994 pp. 155–162.

* cited by examiner

Primary Examiner—Marc S. Hoff
Assistant Examiner—Bryan Bui
(74) Attorney, Agent, or Firm—Jordan and Hamburg LLP

(57) ABSTRACT

A measurement device is disclosed for measuring the conductivity distribution in liquids or multiple phase media flowing in any direction. A grid sensor has electrodes shaped as parallel electroconductive grid bars or wires located in two or three planes and electrically insulated from each other and from their mounting. The electrodes in the individual planes are mutually offset by preferably 90°. One of the planes, the middle plane when three planes are used, forms an exciter plane connected with a pulse generator, whereas the other planes(s) form receiver plane(s) coupled to processing electronics. in the disclosed signal generation process, the electrodes of the exciter plane are successively driven with a symmetrical bipolar rectangular pulse, and all non-driven electrodes are connected with low impedance to the zero potential.

9 Claims, 3 Drawing Sheets

GRID SENSOR FOR DETERMINING THE CONDUCTIVITY DISTRIBUTION IN FLOW MEDIA AND PROCESS FOR GENERATING MEASUREMENT SIGNALS

BACKGROUND OF THE INVENTION

The invention relates to an arrangement for measuring the conductivity distribution in liquids or multi-phase media with any direction of flow, especially for use in chemical engineering and power plant technology. The electrical conductivity is primarily a measure of other physical or chemical properties (such as the volumetric proportion of gas, the concentration, the type of material, etc.) of the liquid or as an indicator of the phase distribution over the measurement cross section of a multi-phase media.

Measurement of electrical conductivity is used increasingly for detenniniz the properties of liquids and multiphase mixtures, such as the proportion by volume of gas. For this purpose, the medium to be measured is energized by direct-current as well as by alternating-current voltage. The evaluation being made by defining the strictly ohmic or complex resistance. Preferably, for this purpose, wire-shaped or planiform electrodes, which are disposed parallel or concentrically to one another, are put into the medium to be measured in laboratory equipment, as well as for large-scale, initial applications. The conductivity is then measured locally, for example, with needle probes (German patent 3,201,799), or integrally between planiform electrodes (German patent 4,041,160). These methods are less suitable for determining the distribution of the local electrical conductivity over a cross section.

Frequently, therefore, tomographic methods of measuring are used for determining the property distribution of liquids or multi-phase systems over a certain cross section. Aside from the use of light radiation or particle radiation with interferometric or hagographic meffiods of evaluation, particularly the use of electrical tomographic methods, with inclusion of electrical conductivity measurements as well as of capacitive measurements, has proven its value. Aside from contactless methods with electrodes at the edge of the flow channel, methods, for which the electrodes are disposed in grid fashion transversely to the direction of flow of the medium (so-called wire mesh sensors), have become established.

In the case of a method developed at the University of Hannover (M. Boddem, N. Reinecke, D. Mewes: "Measurement of two dimensional phase distributions using a wire-mesh sensor", Proc. ECAPT, Oporto, Portugal, 1994 pp. 155–162), parallel wires are disposed in the cross section to be measured in three planes perpendicular to the direction of flow of the mediura and the conductivity between two parallel adjacent wires of a plane is always measured sequentially. The wires of adjacent planes are at an angle of 60° to one another. After all measurements between two parallel adjacent wires of all three planes have been carried out, the projections of the conductivity distribution in the three directions specified by the orientation of tem wire grid are known. From these, the conductivity distribution is determined by means of an extensive tomographic reconstruction algoritbm The additional mathematical calculation of the results of the measurements greatly limits the number of wires that can be handled in practice and the attainable frequency for determining conductivity distributions over a particular cross section.

SUMMARY OF THE INVENTION

It is an object of the present invention to measure the distribution of the conductivity of the flowing Ium with the help of grid sensors without the use of tomographic rcconsion algoriins.

Pursuant to the invention, it is possible to measure with high resolution and high measurement succession the distribution of the electrical conductivity of the flowing medium within the cross section bounded by the grid sensor. The measured values obtained represent the local conductivity values directly and do not require any additional calculation by means of tomographic reconstruction algorithms. For this purpose, a grid sensor with at least two electrode planes is required. With an arrangement in three planes, it is possible, in addition, to follow the movement of inhomnogeneities in the flowing medium, which manifests itself in a change of conductivity, in the flow direction. In a case of a two-phase flow, the velocity of gas particles can thus be measured. A volume section to be considered can be expanded at will by connecting several three plane arrangements in series.

DETAILED DESCRIPTION OF THE INVENTION

For a better understanding the invention is explained m greater detail below by means of examples.

Figure 1:
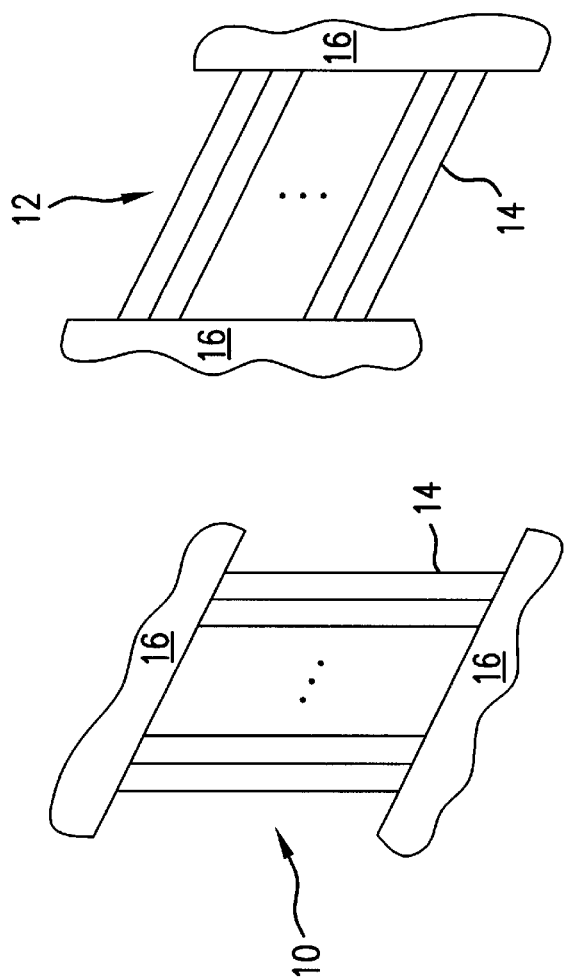
FIG. 1 is a perspective view of grids of a first embodiment of the present invention.

Referring to FIG. 1, for testing purposes, a two-plane grid sensor, having a first grid 10 and a second grid 12, was built for a pipeline with a nominal width of 50 mm with 16 constant an wires per plane as electrodes 14, the wires having a diameter of 0.15 mm. A sensor body includes V2A and the wires insulated with heat-resistant epoxide resin and mounted under tension in a base body 16.

Figure 2:
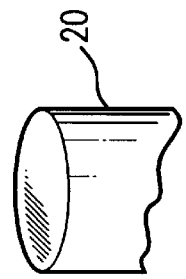
FIG. 2 is a perspective view of an embodiment of an electrode of the present invention.

For industrial use, a two-plane sensor with the electrodes 14 configured as 8 bar-shaped electrodes 20, as shown in FIG. 2, per plane was used for a pipeline with a nominal width of 50 mm, and a two-plane sensor with 16 electrodes per plane was used for a pipeline with a nominal width of 100 mm. To reduce the flow resistance and for strength reasons, the electrodes 20 are lens-shaped, profiled V2A grid bars with a profile thickness of 1.5 mm and a profile length of S mm. The base sensor body 16 includes an electrically conductive material (V2A). The electrodes 20 as grid bars can have a symmetrical profile with respect to a flow direction when flow is reversed.

Figure 3:
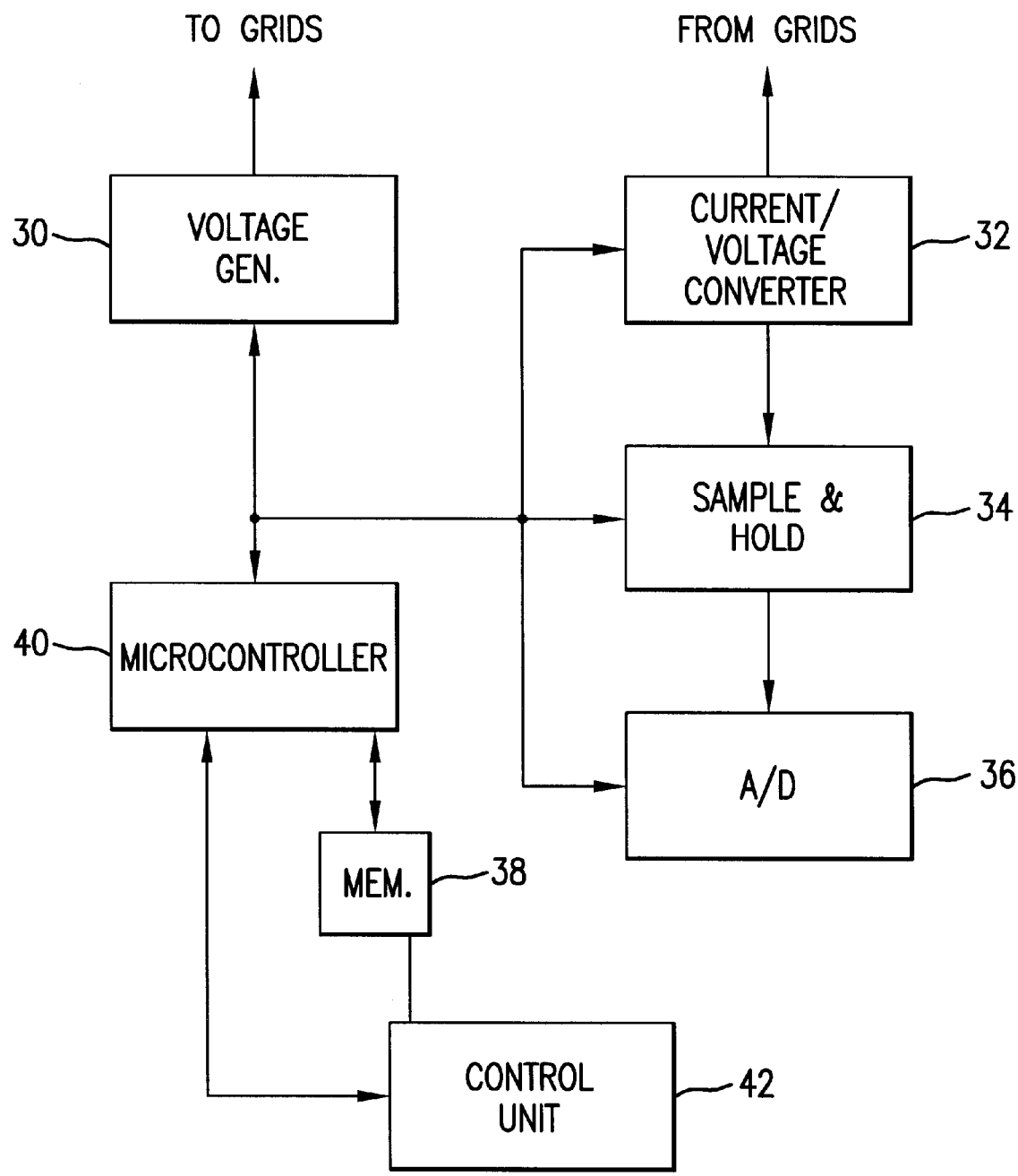
FIG. 3 is a block diagram showing an embodiment of circuitry of the present invent.

Referring to FIG. 3, to energize and evaluate these grid sensors, the following electronic function groups and devices were used. In particular, they are:

energizing voltage generation and excitation 30;

current voltage converter and signal conditioning 32;

sample and hold cirai 34;

analog digital converter 36;

static test result memory 38;

microcontroller 40; and control niit 42.

A measuring process is divided into a number of measurement cycles, equivalent to the number of the energizing electrodes 14 and controlled by a control circuit, i.e., the microcontroller 40, preferably an ASIC. A cycle, which is applied externally at the ASIC and the frequency of which can be programmed, demines the duration of a measurement cycle. For this purpose, the measurement cycle is divided into n partial sections, with which the temporal course of the signal for controlling the measuring and evaluating functions can be programmed The measurement cycles for the individual energizing the electrodes 14 are started successively with respect to time by a counter. The measuring process can be terminated after any number of measuring cycles and started once again, For each measuring cycle, a symmetrical bipolar energizing rectangular pulse ($|+U_{max}|=|-U_{min}|$) is derived from the operating voltages by means of analog switches or an operation amplifier acted upon with an offset voltage at the pulse inlet and applied successively and temporally offset to the energizing electrodes over current-degenerative amplifiers. All nondriven energizing electrodes are connected with low impedance to the zero potential The temporal average value of the energizing rectangular voltage is zero and, with that, to avoid electrolysis effects, the excitation of the grid electrodes 14 is free of DC voltage.

Since the base body 16 is connected to zero potential, the sensor is defined unambiguously with respect to zero potential.

Figure 4:
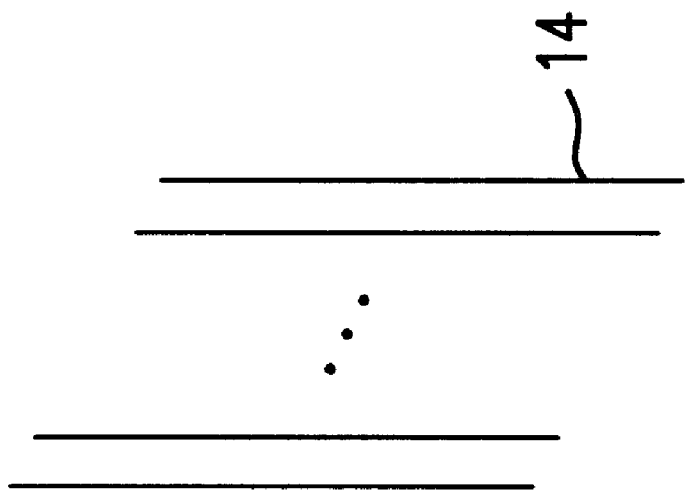
FIG. 4 is a perspective view of grids of a second embodiment of the present invention.
Figure 4:
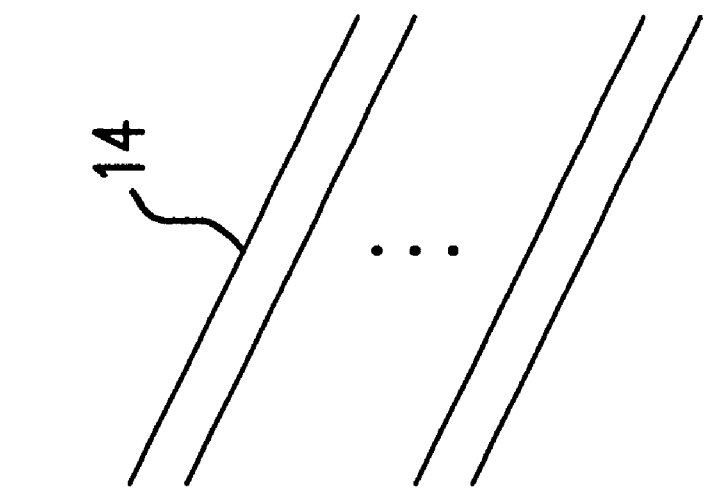
Figure 4:
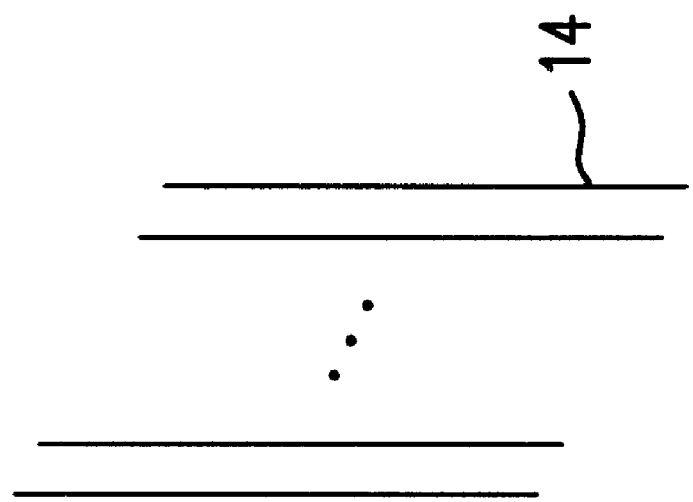

Current entering the electrodes 14 of the receiver plane are converted into voltages by the current/voltage converters 32 with a low input resistance Current measurements on the revving one of the electrodes 14 are evaluated simultaneously for all electrodes of the receiver plane after transient oscillations have decayed. For this purpose, the voltage signals of all evaluation channels are held up to the end of the evaluation at the output of the signal generation with the sample and hold circuits 34. In the case of sensors with three electrode planes, as shown in FIG. 4, a middle plane is connected as an energizer and acts simultaneously on the two adjacent receiver planes.

A method for determining the distribution of electrical conductivity of flowing media using the agd sensor includes a series of steps. The electrodes 14 of the energizing plane arc driven successively with a symmetrical bipolar rectangular pulse, all non-driven electrodes being connected with low impedance to the zero potential. The local conductivity in the immediate surroundings of the crossing point of, in each case, one energizing electrode and one receiving electrode of the electrodes 14 is determined by measuring the current furnished to individual ones of the receiving electrodes 14 at the moment of electrical excitation of the energizing electrode. Measurement of the current entry, as a measure of the local conductivity in the immelate surroundings of all crossing points between in each case an energizing electrode 14 and all receiving electrodes 14, takes place simultaneously. The excitation of the individual energizing electrodes 14 takes place at successive times and the measured current entries at all crossing points are combined to determine a conductivity distribution over the cross section of flowing media.

The measement signals, obtained in the form of electrical voltages, can be evaluated in two different ways. Two possibilities are described in the following:

1. After signals, suitable for the subsequent sample and hold circuits 34, are manufactured, the signal voltages are digitized by the analog to digital converter 36. The transition from the sample state to the hold state takes place simultaneously for all sample and hold circuits. The digitized signal voltages obtained can then be precondensed and stored on an interim basis by means of microprocessors. For the precondensation, the sized measurement results. related to the measurement values of the individual phases of tie medium flowing through, are evaluated. For this purpose, the conductivity of the individual phases ($MW_1$ and $MW_2$) is first measured during a calibration and subsequently, the measured values MW are related thereto, in that a calculated measured value $MW_{calc}=MW_x/MW_2-MW_1/MW_2$.

For the evaluation, a sitedependent evaluation of the values measured (compensating for edge zone effect of the sensor) can be taken into consideration.

2. The signal voltages, prepared in signal manufacturing circuits, i.e. the voltage generator 30, are compared with reference voltages, which correspond to the conductivity of the phase of the multiphase medium having the lesser conductivity. A dual direct statement concerning the condition of the instantaneous phase at the measured site is obtained. It is, however, necessary here to determine and plot the reference voltages at appropriate intervals by means of a measuring unit including an A/D converter, a microprocessor and a D/A converter as a fation of possible temperature changes, concentrations changes, etc. in a sitedependent manner, taking into consideration the edge zone effect.

Whereas the second evaluation possibility can be used predontly for two-phase systems, the first is suitable for universal evaluations.

For following the movement of inhomogeneities in the flowing medium, which manifest themselves in a change in the conductivity in the flow direction, such as the measurement of the velocity or the magnitude of gas particles, several such three-plane sensors are disposed successively and the evaluations of the values measured are synchronized,

What is claimed is:

1. A grid sensor fox deterring a conductivity distribution in flowing media, comprising:

electrodes in the form of one of electrically conductive grid bars and wires, which are disposed perpendicularly to a flow direction, in one of two and three planes, parallel to one another;

a pulse generator;

evaluation electronics;

the electrodes of at least one of the planes being energized by the pulse generator and the electrodes of at least one other plane being coupled to the evaluation electronics for measurement of conductance based on current received by the at least one other plane from the at least one plane;

holding devices for holding said electrodes; and an insulator for insulating the holding devices from the electrodes, wherein adjacent respective ones of said planes have the electrodes disposed at an angle substantially equal to 90° with respect to the eltodes of the adjacent ones of said planes.

2. The grid sensor of claim 1, wherein the electrodes are grid bars and are streamlined.

3. The grid sensor of claim 1, wherein the electrodes are grid bars and have a symmetrical profile with respect to the flow direction when flow is reversed.

4. A method for determining distribution of electrical conductivity of flowing media using a grid sensor comprising the steps of:

providing a plurality of energizing electrodes arranged parallel in a first plane within the flowing media;

providing a plurality of receiving electrodes arranged parallel in a second plane within the flowing media which is displaced and parallel to said first plane, said receiving electrodes being oriented substantially at a 90° angle with respect to said energizing electrodes and connected to a zero potential;

providing a source to drive the energizing electrodes with a symmetrical bipolar rectangular pulse potential;

successively measuring a local conductivity in immediate surroundings of crossing points of individual ones of the energizing electrodes and individual ones of the receiving electrodes by measuring current furnished to the individual ones of the receiving electrodes during successive electrical excitation of the individual ones of the energizing electrodes;

measuring local conductivity in immediate surroundings of all crossing points between individual ones of said energizing electrodes and by measuring current simultaneously furnished to all of said receiving electrodes by the successive electrical excitation of the individual ones of said energizing electrodes; and determining a conductivity distribution over the cross section of the media flow based on the measured currents.

5. The method of claim 4, wherein measurements of the receiving electrodes occur only after a decay of transient electrical oscillations at the electrodes.

6. A grid sensor for determining a conductivity distribution in flowing media, comprising:

electrodes in the form of one of electrically conductive grid bars and wires, which are disposed peiperdicularly to a flow direction, in three planes, parallel to one another;

a pulse generator;

evaluation electronics;

the electrodes of at least one of the planes being energized by the pulse generator and the electrodes of at least one other plane being coupled to the evaluation electronics for measurement of conductance based on current received by the at least one other plan from the at least one plane;

holding devices for holding said electrodes;

an insulator for insulating the holding devices from the electrodes, wherein adjacent respective ones of said planes have the electrodes disposed at an angle substantially equal to 90° with respect to the electrodes of the adjacent ones of said planes; and a middle plane of the three planes is the at least one of the planes coupled to the pulse generator, and outer planes of the three planes are the at least one other plane coupled to the evaluation electronics.

7. A method for determining distribution of eletrical conductivity of flowing media using a grid sensor comprising the steps of:

providing a plurality of energizing electrodes arranged parallel in a first plane within the flowing media;

providing a plurality of receiving electrodes arranged parallel in a second plane within the flowing media which is displaced and parallel to said first plane, said receiving electrodes being oriented to cross said energizing electrodes and connected to a first potential;

providing a source to energize the energizing electrodes with a potential waveform;

successively measuring a local conductivity in immediate surroundings of crossing points of individual ones of the energizing electrodes and individual ones of the receiving electrodes by measuring cod farnished to the individual ones of the receiving electrodes by the energizing electrodes during successive electrical excitation of the individual ones of the energizing electrodes;

measuring local conductivity in imeiate surroundings of all crossing points between individual ones of said energizing electrodes and by measuring current simultaneously furnished to all of said receiving electrodes by the successive electrical excitation of the individual ones of said energizing electrodes; and determining a conductivity distribution over the cross section of the media flow based on the measured currents.

8. The method according to claim 7 wherein said potential waveform is a symmetrical bipolar rectangular pulse.

9. The method according to claim 7 wherein said first potential is a zero potential.

* * * * *